United States Patent [19]
Jeanson et al.

[11] Patent Number: 5,527,315
[45] Date of Patent: Jun. 18, 1996

[54] SPINAL OSTEOSYNTHESIS ROD WITH THREE BRANCHES

[75] Inventors: Jean-Francois Jeanson, Assenay; Thierry Marnay, Nimes, both of France

[73] Assignee: JBS S.A., Troyes Cedex, France

[21] Appl. No.: 325,119

[22] Filed: Oct. 18, 1994

[30] Foreign Application Priority Data

Apr. 21, 1994 [FR] France .................................. 94 04922

[51] Int. Cl.⁶ .................................................. A61B 17/70
[52] U.S. Cl. .................................................. 606/61; 606/73
[58] Field of Search .................... 606/61, 69, 70, 606/71, 72, 73, 60, 104, 53; 623/17

[56] References Cited

U.S. PATENT DOCUMENTS

| | | | |
|---|---|---|---|
| 5,129,899 | 7/1992 | Small et al. | 606/61 |
| 5,234,431 | 8/1993 | Keller | 606/70 |
| 5,261,912 | 10/1993 | Frigg | 606/61 |
| 5,261,913 | 10/1993 | Marnay | 606/61 |
| 5,360,429 | 11/1994 | Jeanson et al. | 606/61 |
| 5,397,363 | 3/1995 | Gelbard | 623/17 |

FOREIGN PATENT DOCUMENTS 528706  2/1993  European Pat. Off. .................. 606/61

Primary Examiner—Guy Tucker
Attorney, Agent, or Firm—Spencer & Frank

[57] ABSTRACT

A device for spinal osteosynthesis includes an elongated bar having two parallel, spaced longitudinal slots extending parallel to the bar length. The slots define a central bar branch and two side bar branches flanking the central bar branch. A plurality of fasteners extend from the bar; each fastener has a shank to be implanted; a head provided at an end of the shank; and a groove provided in the fastener head. The groove has a bottom and divides the head into two leg portions. The central bar branch is received by the groove and is in engagement with the bottom thereof. The leg portions extend through the slots and straddle the central bar branch. A nut is secured to the head of each fastener and abuts a surface of the bar for tightening the fastener to the bar.

5 Claims, 2 Drawing Sheets

27# SPINAL OSTEOSYNTHESIS ROD WITH THREE BRANCHES

BACKGROUND OF THE INVENTION

The present invention relates to a device for spinal osteosynthesis, comprising a strengthened rod with three branches and screws or hooks with cylindrical heads, said rod being arranged in the bottoms of longitudinal grooves of said heads and fixed by screws or nuts.

It is known that rods of circular cross section are generally applied for the spinal ostehosynthesis. The roughness of the surface of such bars is generally increased by serration or indentation. The bars are cooperating with screws or hooks to be implanted, the heads of which are constructed to receive said rod and to be mutually blocked by a nut or screw.

It is also known to connect two vertebrae to each other or one vertebra to the sacrum with plates provided with orificies and screws being screwed into the vertebrae and/or to the sacrum through said orifices.

In the first case, the cross-section of the bar is determined in a way to obtain a certain rigidity and, at the same time, to allow a transverse deformation which enables to compensate some disalignments.

In the second case, the plate has a thickness to allow some deformation in transverse direction meanwhile it has a great rigidity in the lateral direction.

Due to the above circumstances, the rods can change their shape after having been implanted, while the plates are extremely rigid in that direction. Accordingly, no deformation can take place in this respect, which requires, however, a rather high precision in positioning the screws.

SUMMARY OF THE INVENTION

Object of the present invention is to avoid these inconveniences and to provide an improved device for supporting the spine, more particularly for connecting at least two screws or hooks provided with cylindrical heads; said device comprising a rod being indented and having longitudinal grooves wherein the rod and screws are connected by nuts providing for a rigid clamping which enables a certain deformation in a first plane when applying usual means for that purpose though without any deformation in a second plane perpendicular to the first one and to the axis of simmetry of the screw after implantation.

The strengthened rod of the device according to the invention is provided with three branches and screws or hooks with cylindrical heads, said rod being arranged in the bottoms of longitudinal grooves of said heads and fixed by screws or nuts and is provided with two longitudinal slots separated by a central branch, corresponding to the grooves of the cylindrical heads of the screws or the hooks. The slots are bordered by side branches and are of a width corresponding width of the branches on both sides of the grooves in the heads of the screws or hooks. One of the outer surfaces of the central branch corresponds to the bottom of the grooves in the heads of the screws or hooks.

The upper surface of the rod opposite to the one corresponding to the bottom of the groove in the heads of the screws or hooks is knurled.

The lower surface of the rod opposite to the one corresponding to the bottom of the groove in the heads of the screws or hooks is serrated.

The lower surface of the rod opposite to the one corresponding to the bottom of the groove in the heads of the screws or hooks is indented.

The lower surfaces of the side branches are rounded and smooth.

The rod is preferably rounded on both ends and the side walls of the longitudinal slots are rounded on both ends wherein the radius of the rounding is the same as that of the cylindrical heads of the screws or hooks.

At least one edge at the ends of the bar is rounded.

The measures of the side branches are preferably determined by the rigidity to be obtained.

DESCRIPTION OF THE PREFERRED EMBODIMENT

Figure 1:
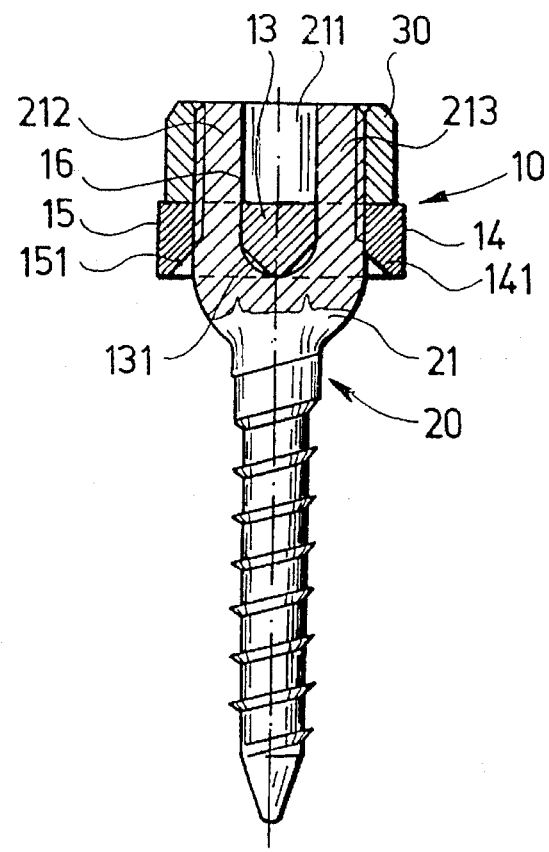
FIG. 1 is the side view of a screw provided with a head and a bar being clamped in the slot of the head by a nut wherein some surfaces of the bar and the screws are indented.

The Figures show a bar 10 provided with slots 11 and 12 which extend along the bar length and which are separated by a central branch 13 and bordered by two side branches 14 and 15. Fasteners such as screws 20 are connected to the bar 10 such that the central branch 13 is received in a slot 211 of each screw 20 and the latter are fixed by nuts 30 abutting on the upper knurled surface 16 of the bar 10.

Figure 2:
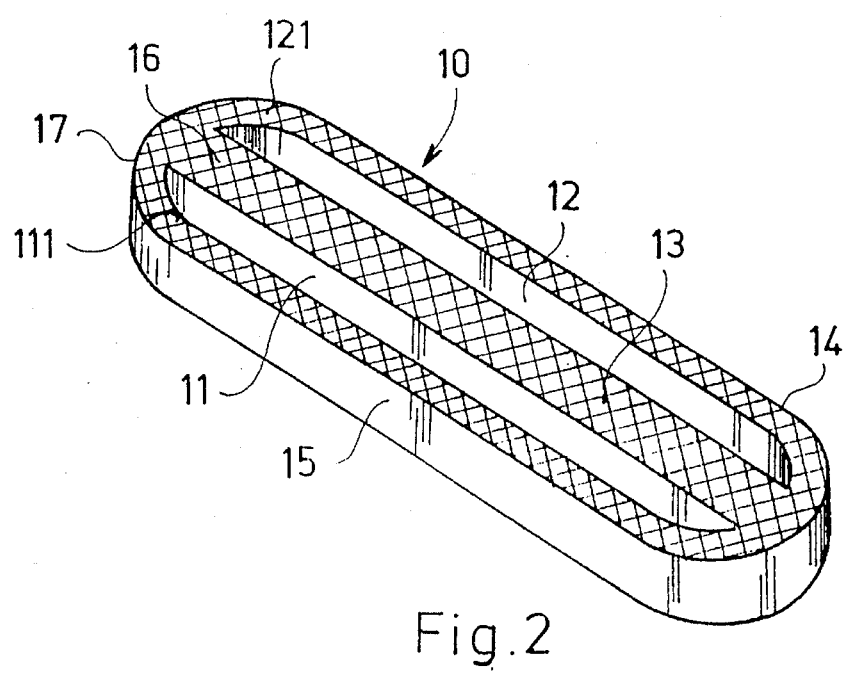
FIG. 2 is a perspective view of the bar according to the invention and FIG. 3 is a perspective view of a bar according to the invention integrated with two screws and nuts.
Figure 3:
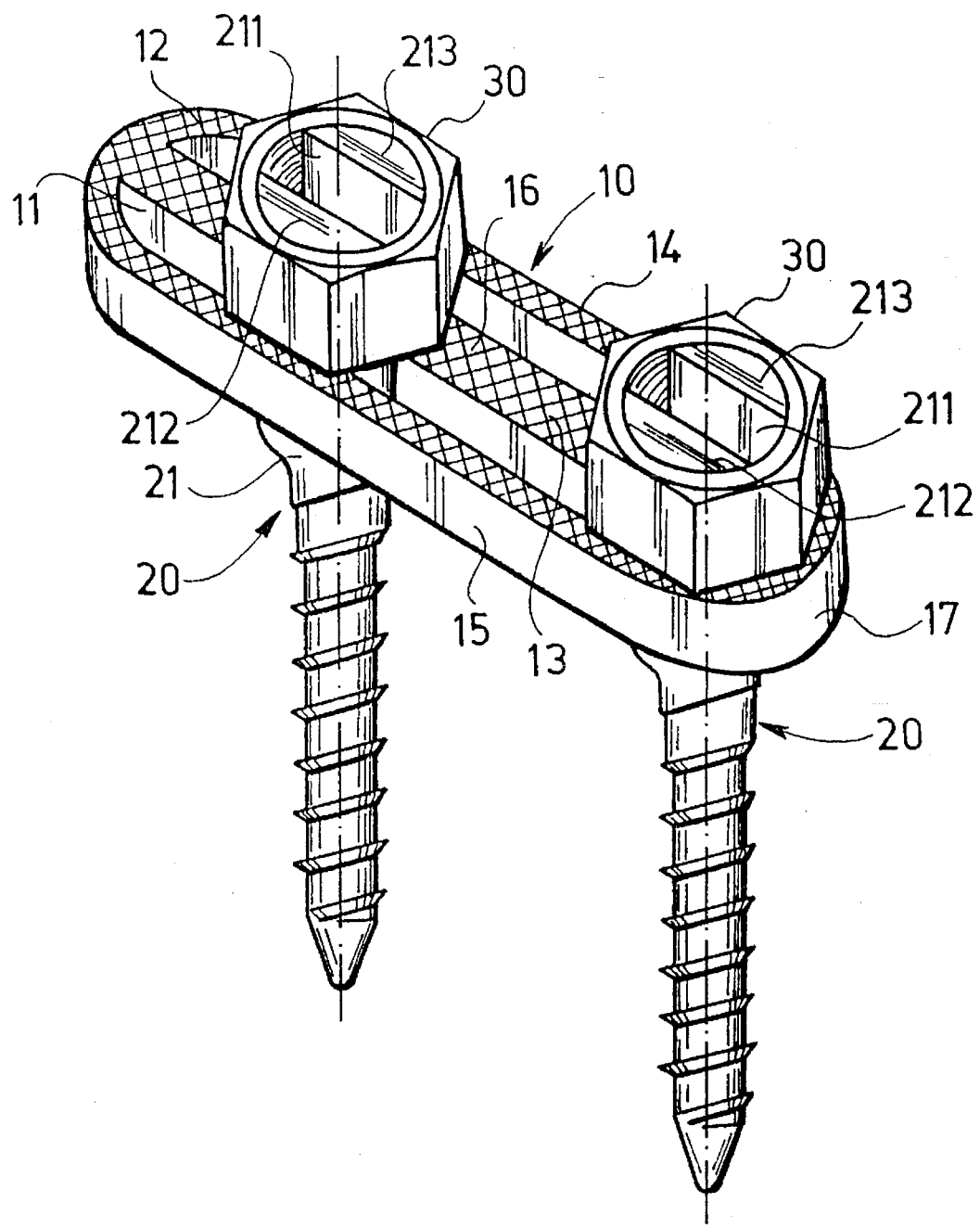

All the details are shown in FIGS. 1 to 3. The central branch 13 of the bar 10 has rounded bottom 131 fitting perfectly to the rounded bottom part of a groove 211 in the cylindrical head 21 of the screw 20. The bar 10 and the screw 20 is firmly connected by said nut 30, the lower surface of which is pressed to the knurled upper surface 16 of the bar. Similar indentation or serration is on the rounded surface 131 of the central branch 13, which also contributes to the firm connection between the head 21 of the screw 20 and the bar 10.

Slots 11 and 12 also have a form fit with the cylindrical head 21 of the screws 20. Accordingly, arcs 111 and 121 are provided at both ends of the slots 11 and 12; said arcs having the same radius as that of the cylindrical 21 head of the screws 20. The cylindrical head 21 of the screw 20 is in this way totally embraced by the inner surface of the slots 11 and 12 at the extreme positions within the bar 10.

It is to be noted that the inner parts of the lower surfaces of the side branches 14 and 15 have a rounded form 141 and 151 which enables an easy insertion of legs 212 and 213 defining the groove 211 in head 21 of the screw 20 into the slots 11 and 12 of the bar 10. The outer edges of the side branches 14, 15 could also be rounded, if needed, in order to avoid traumatic effects.

FIG. 3 shows how bar 10 with branches 13, 14 and 15 receives screws 20 which have already been screwed into the adjacent vertebrae, indepently from the distance between the screws 20 as a continous adjustment of the distance may be obtained along the whole length of the slots 11 and 12 in order to obtain a fixing, elongation or compression of two vertebrae of a spine.

The rounded form of the lower face of the centrally, branch 13 according to the drawing is only for the sake of example to conform to the shape of the slot in the head of the screw applied. It can of course be produced in many other possible forms.

The connection between the bar and the screws or hooks provided with cylindrical, slotted heads wherein nuts are provided for fastening the screws or hooks, other means for fixing the parts together can also be applied: a screw can e.g. clamp the bar in the slot of the screw by axial movement in said slot and then the inner side walls of the slot in the head of the screw can be provided with an indentation. Moreover, any other form of the implant screws or hooks can be applied within the scope claimed in the attached claims.

We claim:

1. A device for spinal osteosynthesis, comprising
   (a) a bar having a length dimension; said bar having two parallel, spaced longitudinal slots extending parallel to said length dimension and defining a central bar branch and two side bar branches flanking said central bar branch;
   (b) a plurality of fasteners extending from said bar; each fastener having
      (1) a shank to be implanted;
      (2) a head provided at an end of said shank;
      (3) a groove provided in said head; said groove having a bottom and dividing said head into two leg portions; said central bar branch being received by said groove and being in engagement with said bottom thereof; said leg portions extending through said slots and straddling said central bar branch; and
   (c) a separate nut secured to said head of each said fastener and abutting a surface of said bar; each said nut tightening a respective said fastener to said bar.

2. The device as defined in claim 1, wherein said surface of said bar is knurled.

3. The device as defined in claim 1, wherein said side bar branches have bottom surfaces opposite said surface of said bar; and further wherein said bottom surfaces are rounded and smooth.

4. The device as defined in claim 1, wherein said bar is rounded at opposite ends thereof.

5. The device as defined in claim 1, wherein said head is cylindrical and wherein said longitudinal slots have side walls rounded on opposite ends with a radius of curvature equalling a radius of the cylindrical head.

* * * * *